(12) United States Patent
Srivastava et al.

(10) Patent No.: US 10,874,382 B2
(45) Date of Patent: Dec. 29, 2020

(54) MOTORIZED SURGICAL INSTRUMENT (71) Applicant: Sudhir Srivastava, Midland Texas, TX (US)

(72) Inventors: Sudhir Prem Srivastava, Frisco, TX (US); Sugumar Perumalsamy, Madurai (IN); Dan Wallace, Santa Cruz, CA (US)

(73) Assignee: SS INNOVATIONS CHINA CO., LTD., Zhejiang (CN)

( * ) Notice: Subject to any disclaimer, the term of this patent is extended or adjusted under 35 U.S.C. 154(b) by 440 days.

(21) Appl. No.: 15/038,478

(22) PCT Filed: Nov. 21, 2014

(86) PCT No.: PCT/IB2014/066250
§ 371 (c)(1),
(2) Date: May 23, 2016

(87) PCT Pub. No.: WO2015/075689
PCT Pub. Date: May 28, 2015

(65) Prior Publication Data
US 2016/0296219 A1 Oct. 13, 2016

(51) Int. Cl.
A61B 17/00 (2006.01)
A61B 34/00 (2016.01)
A61B 34/30 (2016.01)
A61B 17/29 (2006.01)

(52) U.S. Cl.
CPC ........ *A61B 17/00234* (2013.01); *A61B 34/30* (2016.02); *A61B 34/71* (2016.02); *A61B 17/29* (2013.01); *A61B 2017/00398* (2013.01); *A61B 2017/00477* (2013.01); *A61B 2034/305* (2016.02); *A61B 2034/715* (2016.02)

(58) Field of Classification Search
CPC ........ A61B 2034/715; A61B 17/00234; A61B 34/71; A61B 34/30; A61B 2017/00398; A61B 2034/305; A61B 17/29; A61B 2017/00477
See application file for complete search history.

(56) References Cited

U.S. PATENT DOCUMENTS

| | | | | |
|---|---|---|---|---|
| 5,482,054 A | * | 1/1996 | Slater | A61M 1/0064 600/564 |
| 2002/0111621 A1 | * | 8/2002 | Wallace | A61B 34/71 606/41 |
| 2013/0184690 A1 | * | 7/2013 | Doyle | A61B 34/70 606/1 |

* cited by examiner

Primary Examiner — Michael W Kahelin (57) ABSTRACT

In one embodiment of the invention, a motorized surgical instrument including an elongated shaft, a wrist member and a pair of working members with at least one working member moveable relative to other working member between open and closed position, is presented. The elongate shaft includes towards its proximal end a carriage plate that enables independent and controlled motion of the surgical instrument employing plurality of actuators securely held therein. Further, disclosed is a surgical instrument enabling easy and quick replacement of working members.

35 Claims, 10 Drawing Sheets

MOTORIZED SURGICAL INSTRUMENT

FIELD OF THE INVENTION

The present disclosure relates in general to surgical instrument that augments surgeon's ability to perform minimally invasive procedures, and more particularly to advanced surgical instruments capable of exhibiting enhanced surgical performance with independent control of motion during the surgical procedure.

Furthermore, the disclosure relates to surgical instrument having replaceable tool tips facilitate substituting a more appropriate tool tip for a "previous one" for performing a different function or similar function more precisely.

BACKGROUND OF THE INVENTION

Minimally invasive surgical procedure has successfully replaced conventional surgery by making it less traumatic with significantly reduced incision size through which the surgical instrument is inserted. In existing robot-assisted surgical procedures, the surgical instrument driving unit is usually mounted on the manipulating robotic arm to rotate the instrument about the instrument axis and end effectors about the pivotal connection which offers disadvantages that may hamper the progress of minimally invasive surgery.

The currently prevailing minimally invasive surgical technology is therefore constrained in its applicability as it involves an assembly of colossal manipulating means to effectuate articulation of the surgical instrument at the surgical site. Since the motion of the surgical instrument is driven by driving units mounted on the manipulating robotic arms, the surgical instrument is configured to adapt itself only to manipulators accommodating such complementing arrangements of driving unit. There is a limitation to the configurations possible with only this configuration, of which limited dexterity and minimal mobility are the most formidable challenges cited by the surgeons. The surgical instrument, thus, is not rendered independently functional, meaning the given configuration requires accompanying set up to achieve basic functionality thereby limiting functionality. Further, there has been always a need to establish mechanical and electrical connections to transmit physical motion to the surgical instrument, thus requiring arduous disassembly and reassembly procedures.

Moreover, in robotic surgical field, the surgical instruments that are mounted to perform the surgery are usually disposed off after one single use, or are repeatedly sterilized after each single use. As acknowledged by those skilled in the art that the tips of these surgical instruments, primarily forceps or gripper that remains attached to the distal end of the surgical instrument for performing the surgery get degraded by the use of plurality of times thereby providing a possibility that malfunction occurs in use by this degradation.

In view of aforementioned limitations what is needed therefore is a surgical instrument enabling precise control over the end effectors through the use of control drive elements of the instrument that can make the instrument get employed with different manipulating medical arms used in the industry today; hence simplifying the control arrangement with consequent cost savings. Also, needed is a surgical instrument that allows easy replacement of surgical instrument tips which may facilitate easy sterilization process thereby further cutting exorbitant cost involved in replacing the entire surgical instrument after few surgical use.

The foregoing discussion is intended only to illustrate some of the shortcomings present in the field of the invention at the time, and should not be taken as a disavowal of claim scope.

SUMMARY OF THE INVENTION

In connection with the general aspects of various embodiments of the present invention, there is provided a surgical instrument that at least in one form, comprises a longitudinal shaft having shaft axis defining a proximal end and a distal end, said shaft configured to be rotatable about the shaft axis in response to the actuation motion thereto. The elongated shaft operably couples to a wrist member at its distal end by a pivotal connection defining a wrist axis. The wrist member is configured to be angularly displaceable about the wrist axis by at least two wrist member-moving actuators that are operatively coupled to a single continuous wrist member-moving elongate element such that selective pulling of one end of the elongate element causes concomitant movement of the wrist member therewith in one direction while counter-pulling causes movement of the wrist member in opposed other direction.

Further, towards the working end of the wrist member is provided a pair of working members: a first working member and a second working member coupled by a common pivotal connection to wrist member to define working member axis, and the working members being configured to be displaced angularly about the working member axis when independently actuated by first working member-moving actuator coupled with corresponding first working member-moving elongate element or second working member-moving actuator coupled with corresponding second working member-moving elongate element respectively.

In connection with yet another general aspect of one form of the present invention, the shaft rotating actuators, wrist member-moving actuators and the working member-moving actuators are sterilizable, and are configured to generate a plurality of discrete motions of the shaft, the wrist member and the working members upon application of actuation motions thereto.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the various forms of the present invention.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a patient-side assistant manipulating the casing portion or carriage plate end of the surgical instrument. The term "proximal" referring to the portion closest to the patient side assistant and the term "distal" referring to the portion located away from the assistant and towards the patient. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

In one further aspect of the invention, the surgical instrument is releasably secured to the robotic arm using any suitable releasable attachment means or interface. Thus unlike, in standard robotically-assisted surgery wherein the operational position of surgical instrument is controlled by a drive assembly enclosed within the housing of robotic arm and requires proportional coordinated movements between the surgical instrument and the articulated arm; the present disclosure is particularly useful for controlling the surgical instruments at the surgical site independent of the relative proportional movements of the entire robotic arm. This is achieved by involving surgical instrument of modular construction, as will be explained later.

Figure 1:
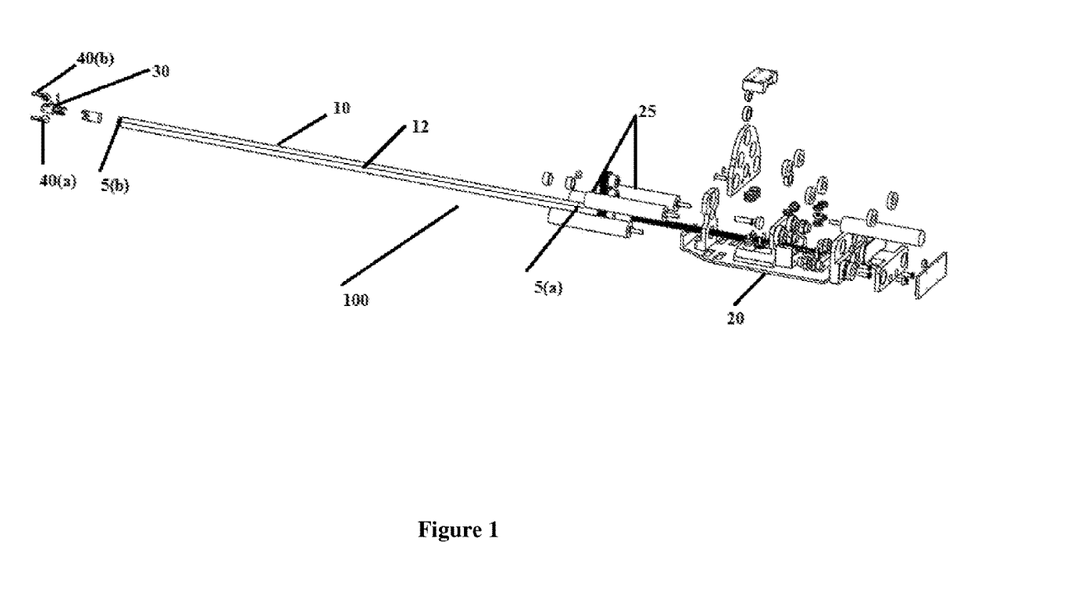
FIG. 1 is an exploded perspective view of one form of surgical instrument in accordance with an embodiment of the present invention.

Reference is now made to FIG. 1 wherein one form of a surgical instrument 100, in accordance with first preferred embodiment of the present invention is illustrated. In at least one embodiment, the surgical instrument 100 includes a carriage plate assembly 20 that is attached to an elongated shaft assembly 10 that is configured for operable attachment to a variety of different surgical tool heads or working members 40(*a*) and 40(*b*).

FIG. 1 illustrates an exploded view of the surgical instrument 100 comprising a wrist member assembly 30 coupled towards its working end with different working members 40(*a*) and 40(*b*), the attachment and operation of which will be discussed in further detail below. In the depicted embodiment, the carriage plate assembly 20 operably supports an actuation system generally designated as 25 which is configured to selectively apply various forms of actuation motions to the particular-type of working members, commonly designated as 40, attached thereto. As the present detailed description proceeds, those of ordinary skill in the art will appreciate that surgical instrument 100 disclosed herein may be configured to operably interface with a robotic control system that can provide the requisite control signals to actuate actuating system 25 present within the instrument 100.

In the given embodiment, all practical motions of surgical instrument 100, namely the rotational movement of the instrument about its axis, rotation of the wrist member 30, and opening and closing action of the working members 40 or their rotation independent of each other, are power implemented by the instrument's actuators and gear assembly housed in its carriage plate 20.

It is to be understood that further degrees of motion are also possible, such as angular tilt in any direction, freely movable in space; however such further degrees of freedom are likely to be largely limited in practice by the constrained surgical environment in which the surgical instrument 100 is being used. A combination of all these motions enables a high level of flexibility to be accomplished with this surgical instrument 100, with added advantage of better control as movement is distantly dictated by surgeon's hand. Further details of the operational characteristics of the surgical instrument 100 and specialized instrument architecture designed to achieve the same are given hereinbelow in FIGS. 1-8, and associated description.

In various embodiments, the carriage plate assembly 20 cooperatively engages with the proximal end 5(*a*) of the elongated shaft 10 that extends along the shaft axis 12 and includes an actuating system 25 that may be fixedly held therein by suitable fastening arrangements for ease of assembly. The elongated shaft 10 includes an outer shaft casing that forms substantially a hollow conduit. The outer shaft casing has a proximal end 5(*a*) that is rotatably coupled to the carriage plate assembly 10 and an open distal end 5(*b*) to engage the wrist member 30 and pair of working members 40(*a*) and 40(*b*). The instrument 100 is typically releasably mounted to a robotic arm by means of an interfacing member. To be suitable for minimally invasive surgery the surgical instrument must be operable about axis that intersect at the orifice through which the instrument is inserted into the patient.

It is to be appreciated that the field of application of the invention is not limited to surgical procedures at internal surgical sites only, but can be used on open surgical sites as well.

Re-referring to FIG. 1, a disassembled view of the surgical instrument 100 is presented that includes a unique and novel transmission or actuation system, all housed within the carriage plate 20 to facilitate different motions of the instrument 100 required to perform surgical procedures including roll motion of the shaft 10 about the shaft axis 12, wrist-like motion of the wrist member 30 about the wrist axis, and scissor like motion of the working members 40(*a*) and 40(*b*) about the working member axis, wherein the working members can be displaced angularly about the working member axis independently of the other, so that the working members, together as a whole 40, is angularly displaceable.

Figure 2:
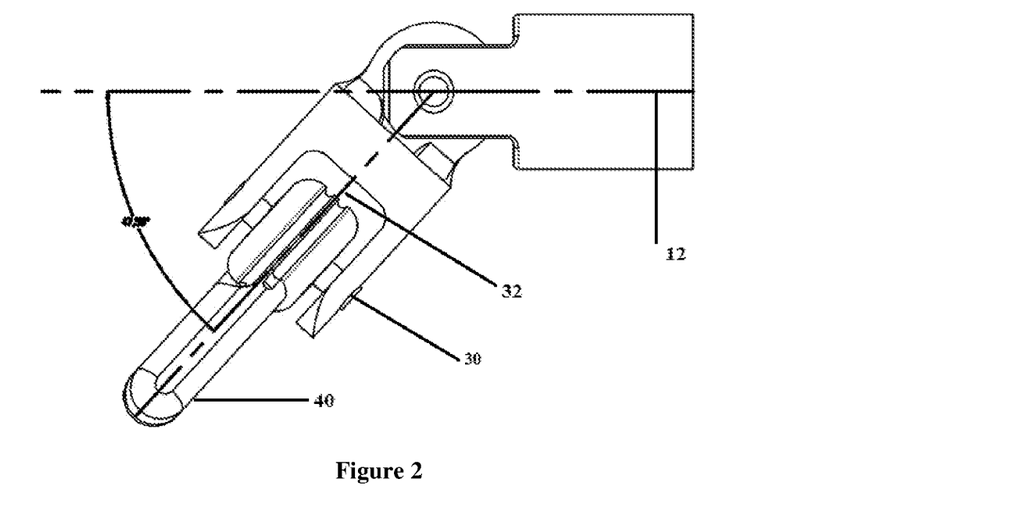
FIG. 2 is an exploded perspective view of wrist member of the surgical instrument in accordance with an embodiment of the present invention.

As best can be seen in FIG. 1 in combination with FIG. 2, it will be appreciated that the wrist member 30 is coupled to the distal end 5(*b*) of the shaft 10 by a pivotal connection to define a wrist axis 32 about which the wrist member 30 exhibits wrist like motion as it gets angularly displaced in either direction. Likewise, the working members 40(*a*) and 40(*b*) are pivotally mounted to the opposed working end of the wrist member 30 to pivot about the working member axis defining a scissor like arrangement. It will be appreciated that the working members 40 can be in the form of any required surgical tool having two members or fingers which pivot about a common pivotal axis, such as scissors, pliers for use as needle drivers, any electrocautery instruments or the like.

The wrist member axis 32 remains non parallel, and substantially perpendicular to the shaft axis 12 thereby permitting wrist member 30 to rotate relative to the shaft axis 12 around two substantially orthogonal axis. Likewise the wrist member axis 32 and the working member axis also remain non parallel, and substantially orthogonal to each other. It has to be noted that the free ends of the working members 40 are angularly displaceable about the working member axis 32 towards and away from each other in a scissor-like fashion, independently of each other, such that the working member 40 as a whole is displaceable in either direction.

Figure 3:
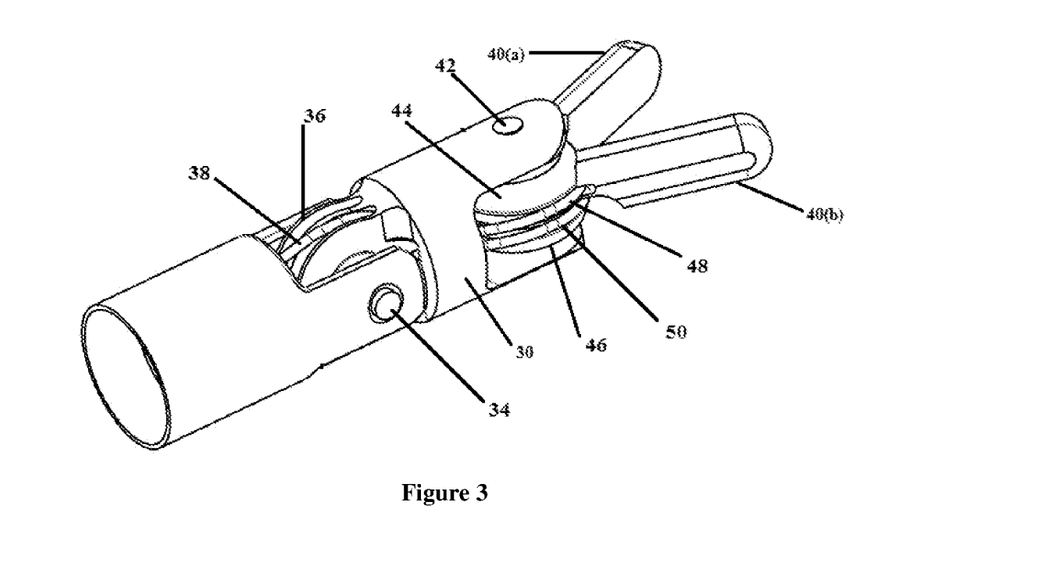
FIG. 3 is view illustrating functional aspects of the wrist member and the working members in accordance with and embodiment of the present invention.

Referring to FIG. 3 and also to FIG. 2, the wrist member axis 32 have disposed thereupon a pulley means 36 defining a circumferentially extending channel to wound thereon a wrist-member moving elongate element 38 that extends towards the proximal end 5(*a*) of the shaft 10, as described in greater detail now. As can be seen in FIG. 3, the pulley means 36 includes a centrally disposed hole through which the pivotal pin 34 extends to establish a pivotal connection of the wrist member 30 with the elongated shaft 10. With reference to FIG. 3, the working member axis is flanked by two set of pulleys 44 and 46 which are coaxially positioned on the pivotal connection 42 to be generally co-planar relative to each other.

Similar to the pulley means 36 of the wrist member 30, each pulley 44 and 46 defines a circumferentially extending channel to receive the respective working member-moving elongate elements 48 and 50 that extends towards the proximal end 5(*b*) of the shaft 10. The working member-moving elongate elements 48 and 50 snugly pass through a slot provided on the wrist member 30 before they join with wrist-member moving elongate element 38 in their travel through the hollow conduit of shaft 10 towards its proximal end 5(*a*).

Reference is now made to FIG. 4-8, according to a further preferred embodiment, the inside view of carriage plate 20 showing a preferred arrangement of actuating system 25 and elongate elements for generating movements needed for the instrument to function, is presented. As can be clearly seen in FIG. 4, the carriage plate assembly 20 has been compartmentalized by two upright support members 62 and 82 extending upwardly from horizontally laid carriage plate 20 to apparently form three compartments therein.

The first compartment 60 of the carriage plate 20 is separated from second compartment 70 by a support column 62 held in an upright position perpendicular to the carriage plate 20. The first compartment 60 is configured to engage a gear assembly 64, shown in FIG. 8, as will be discussed in greater detail below. Such gear assembly 64 operably couples with the elongated shaft 10 to permit rotation of the shaft about the shaft axis 12. More specifically and with reference to FIG. 8, the gear assembly 64 includes a stack assembly of three gears 64(*a*), 64(*b*) and 64(*c*), preferably spur gears having gear ratio of at least 1:1, being configured to meshingly engage with each other and rotate in unison to generate desired power for shaft rotation. Though, a single gear may also replace the present embodiment of three gears in gear assembly 64, it will however occupy larger workspace and will deviate from the idea of conserving space within the carriage plate 20, much desired to make the instrument independently movable relative thereto.

Figure 4:
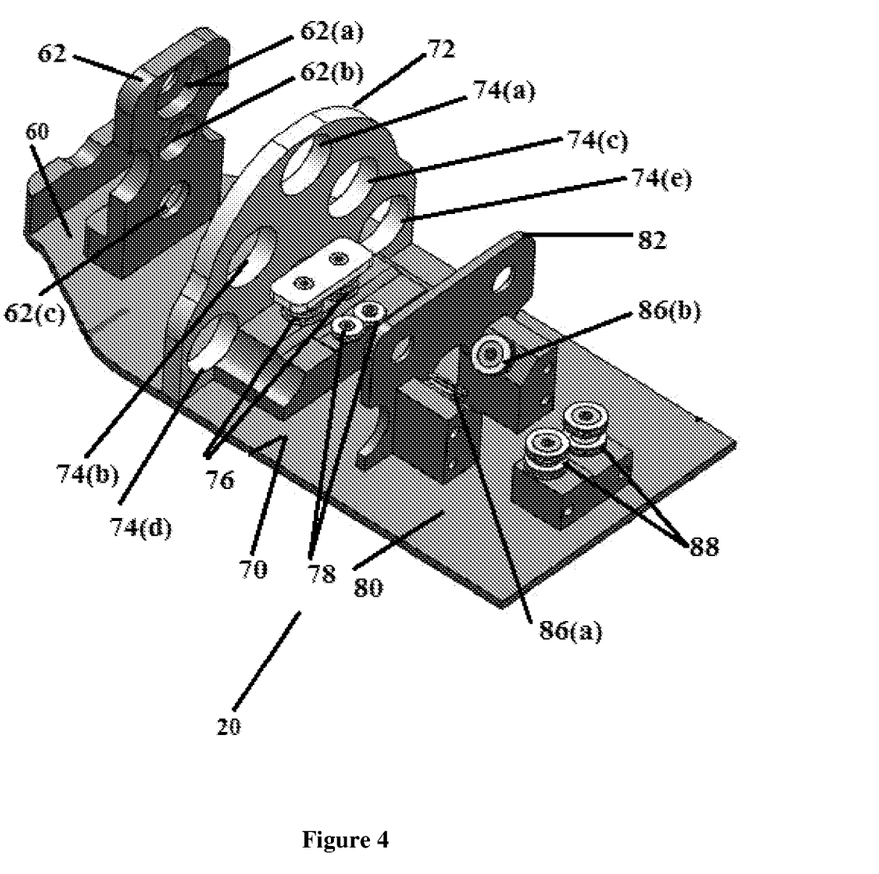
FIG. 4 is a simplified perspective drawing showing the carriage plate with various guiding mechanisms in accordance with an embodiment of the present invention.
Figure 5:
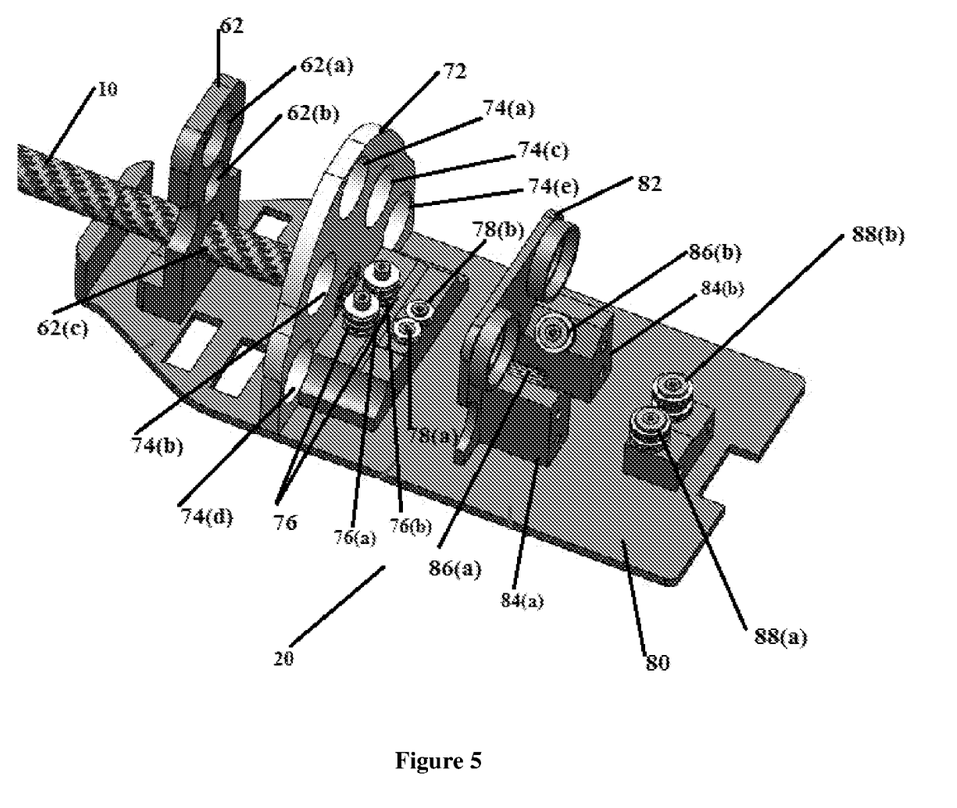
FIG. 5 illustrates one other view of the carriage plate coupled to the elongated shaft in accordance with an embodiment of the present invention.

Referring to FIGS. 4 & 5, and as was discussed above, the support column 62 defining boundaries of first compartment 60, includes vertically spaced openings 62(*a*), 62(*b*) and 62(*c*), wherein opening 62(*a*) is configured to receive shaft rotating actuator 25(*a*) that axially extends therethrough and operably cooperates with the gear assembly 64 to result in rotational movement of the surgical instrument 100 about the shaft axis 12. The opening 62(*b*) engages with a support shaft 66, generally provided to support the central gear 64(*b*) of the stack gear assembly (shown in FIG. 8), and the opening 62(*c*) sized and shaped to receive the elongated shaft 10.

Referencing to FIG. 4-8, one form of actuation system 25 within the carriage plate 20 includes a bracket plate 72 adapted for fixed securance to the second compartment 70 defined in the carriage plate 20, to support the actuating system 25. The actuating system 25 comprising plurality of actuators, particularly the shaft actuating actuator 25(*a*), at least two wrist member-moving actuators 25(*b*), 25(*c*), first working member-moving actuator 25(*d*) and second working member-moving actuator 25(*e*) that extends through plurality of spaced apart slots 74(*a*), 74(*b*), 74(*c*), 74(*d*), 74(*e*) provided on the bracket plate 72 that are sized to receive actuators 25 of suitable proportion and dimensions.

Figure 8:
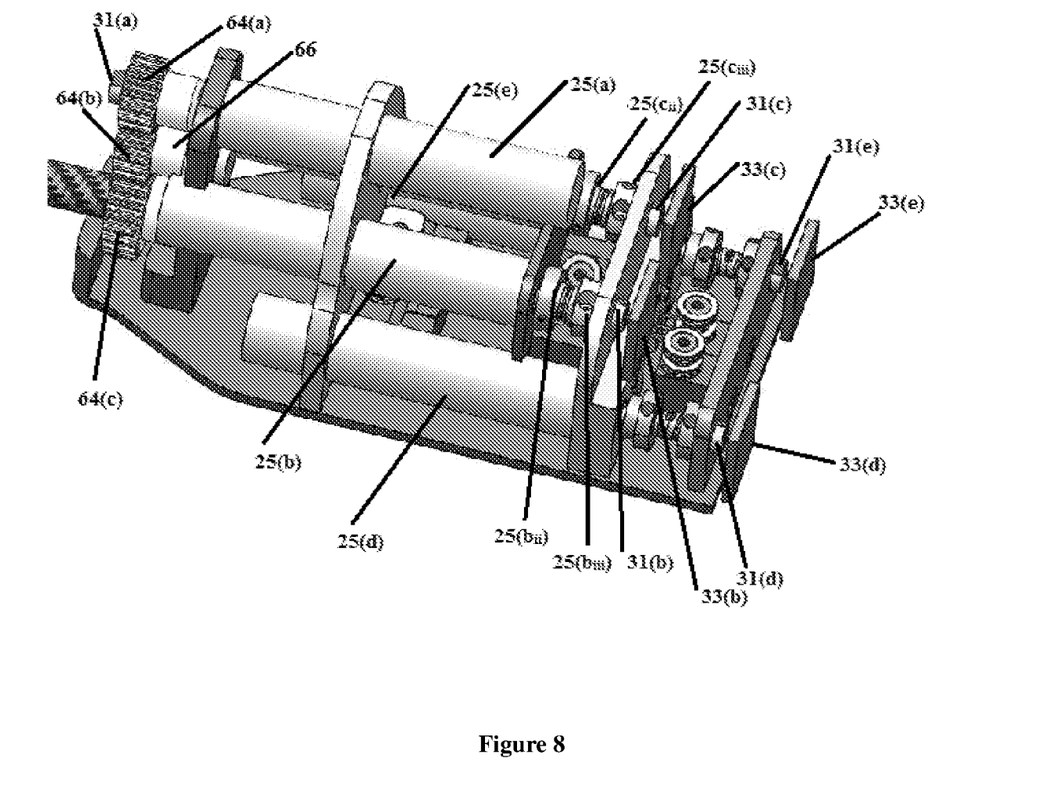
FIG. 8 is a top view of the carriage plate housing actuators and a gear assembly in accordance with one embodiment of the present invention.

As depicted in FIG. 8, in one specific, but not limiting embodiment, the shaft rotating actuator 25(*a*) extending axially through top-most opening 62(*a*) of the support column 62 advances through the slot 74(*a*), the two wrist member-moving actuators 25(*b*) and 25(*c*) advances through 74(*b*) and 74(*c*) and first working member-moving actuator 25(*d*) and second working member-moving actuator 25(*e*) advances respectively through slots 74(*d*) and 74(*e*). One of skill in the art will recognize that plurality of actuators 25 advancing through given slots on the bracket plate 72 shall not be construed limiting in sense that any actuator may be allowed to advance through any slot depending on the pattern in which one desires to lay the network of elongate elements. Further combinations of above embodiment may be gleaned by person skilled in art, and hence is not discussed separately in the present disclosure.

As previously described, the second compartment 70 is separated from the third compartment 80 by a second uprightly extending support column 82. As can be seen in FIG. 4-7, the support column 82 includes two spaced apart openings to receive respectively the two wrist member-moving actuators 25(b) and 25(c) protruding from the bracket plate 72. In one embodiment, the support column 82 further defines towards its peripherals a pair of arcuate slots to receive respectively the first working member-moving actuator 25(d) and second working member-moving actuator 25(e), also protruding from afore-mentioned bracket plate 72. However, those ordinary skills in the art will appreciate that the support column 82 can be designed like any other support column including spaced apart openings to receive and hence support actuator assembly such that requisite space is conserved for each actuator for free actuated motion, thus also allowing instrument to be of minimum size and weight.

Turning to FIGS. 4 and 5 again, a preferably raised platform raised right angularly from the carriage plate 20 and well-suited for supporting and securing an urging arrangement 76 and a channeling structure 78 is presented. Such an urging arrangement 76 comprises a pair of spaced apart composite pulley assemblies 76(a) and 76(b), each assembly further comprising a set of three idler pulleys— $76(a_i)$, $76(a_{ii})$, $76(a_{iii})$ and $76(b_i)$, $76(b_{ii})$, $76(b_{iii})$ (not individually marked and shown in Figure) arranged in a stacked fashion such that bottommost pulleys of each set $76(a_{iii})$ and $76(b_{iii})$ are secured fixedly to the platform, engaging thereupon central pulleys $76(a_{ii})$ and $76(b_{ii})$, that further bears securely thereupon topmost idler pulleys $76(a_i)$ and $76(b_i)$. The channeling structure 78 hereinfore mentioned includes a first guide pulley 78(a) and second guide pulley 78(b) maintained in a suitably oriented plane, but different, preferably lower, from that of the urging arrangement 76. It has to be noted that the set of idler pulleys are provided further with a pair of ball bearings.

As can be seen in FIG. 5, the third compartment 80 of the carriage plate 20 comprises a pair of oppositely disposed side columns 84(a) & 84(b), disposed in generally vertically upstanding relation in respect to the carriage plate 20, and inclined at surface facing towards each other so as to mount upon the inclined surface a first guiding mechanism 86 comprising a pair of guide pulleys 86(a) and 86(b) that are positioned at a requisite angle with respect to shaft axis 12. Preferably, the angles are maintained between 30 degrees to 65 degrees relative to centrally extending shaft axis 12. These idler pulleys are provided with ball bearings as above.

As is further depicted in FIG. 5, an L-shaped raised platform is provided in the third compartment 80 to support the second guiding mechanism 88 comprising a set of idler pulleys 88(a) and 88(b) supported with a pair of ball bearings, each set further comprising a set of at least two pulleys $88(a_i)$, $88(a_{ii})$, $88(b_i)$ and $88(b_{ii})$ (not individually shown in Figure) laid in a stacked configuration. The L-shaped configuration the platform positions one set of idler pulley in a plane higher than the other for the reasons as illustrated in greater detail now.

As indicated above, the working member-moving elongate elements 48 and 50 along with wrist-member moving elongate element 38 travel through the hollow conduit of shaft 10 towards its proximal end 5(a). Thus, each elongate element forming two sides of each single continuous elongate element as 38(a), 38(b), 48(a), 48(b), 50(a) and 50(b), and totaling to six travels the length of shaft 10 that extends up to the second compartment 70. Now, six elongate elements entering the second compartment 70 of carriage plate 20 are urged through the urging arrangement 76 so that the elongate elements remain closer to each other, and hence the shaft axis 12. In one embodiment, the elongate elements are kept at a distance of not more than 1.4 mm from each other.

Figure 6:
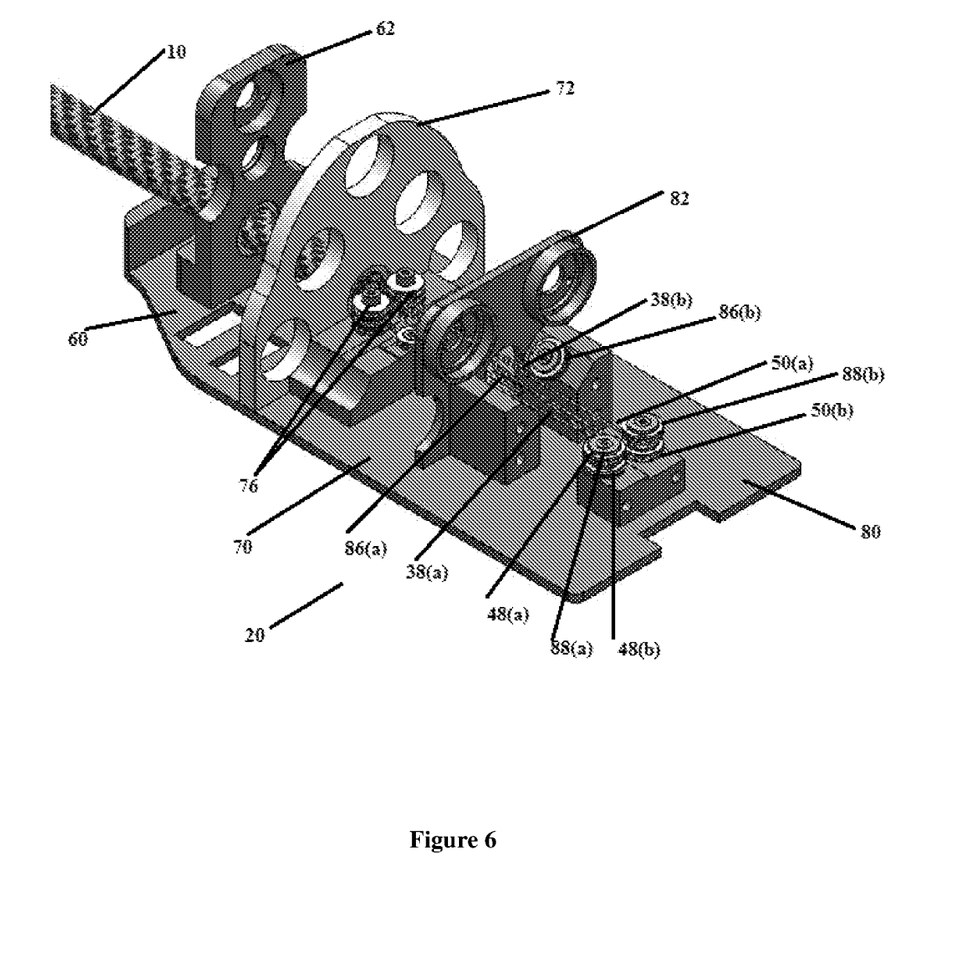
FIG. 6 illustrates another perspective view of the carriage plate with elongate members laid over the guiding mechanisms in accordance with an embodiment of the present invention.

As shown in FIG. 6, the first working member moving elongate element 48 engaging pulley means 44 at the working member axis at distal end, returns along the length of shaft 10 and urged through the urging arrangement 76 to engage topmost idler pulley $76(a_i)$ with its one end 48(a), while the other end 48(b) engages the bottommost pulley $76(b_{iii})$ of second composite pulley assembly 76(b). Likewise, the second working member moving elongate element 50 engages another pulley means 46 coaxially positioned at the working member axis, returns along the length of shaft 10 and urged through the urging arrangement 76 to engage topmost idler pulley $76(b_i)$ with its one end 50(a), while the other end 50(b) engages the bottommost pulley $76(a_{iii})$ of first composite pulley assembly 76(a).

The wrist member-moving elongate element 38, on the other hand rides over the pulley means 36 disposed at the wrist member axis 32, over its circumferential channel, gets pulled backwards to run through the shaft 10, urge through the urging arrangement 76 to engage its two free ends 38(a) and 38(b) with central idler pulleys $76(a_{ii})$ and $76(b_{ii})$ respectively.

Figure 7:
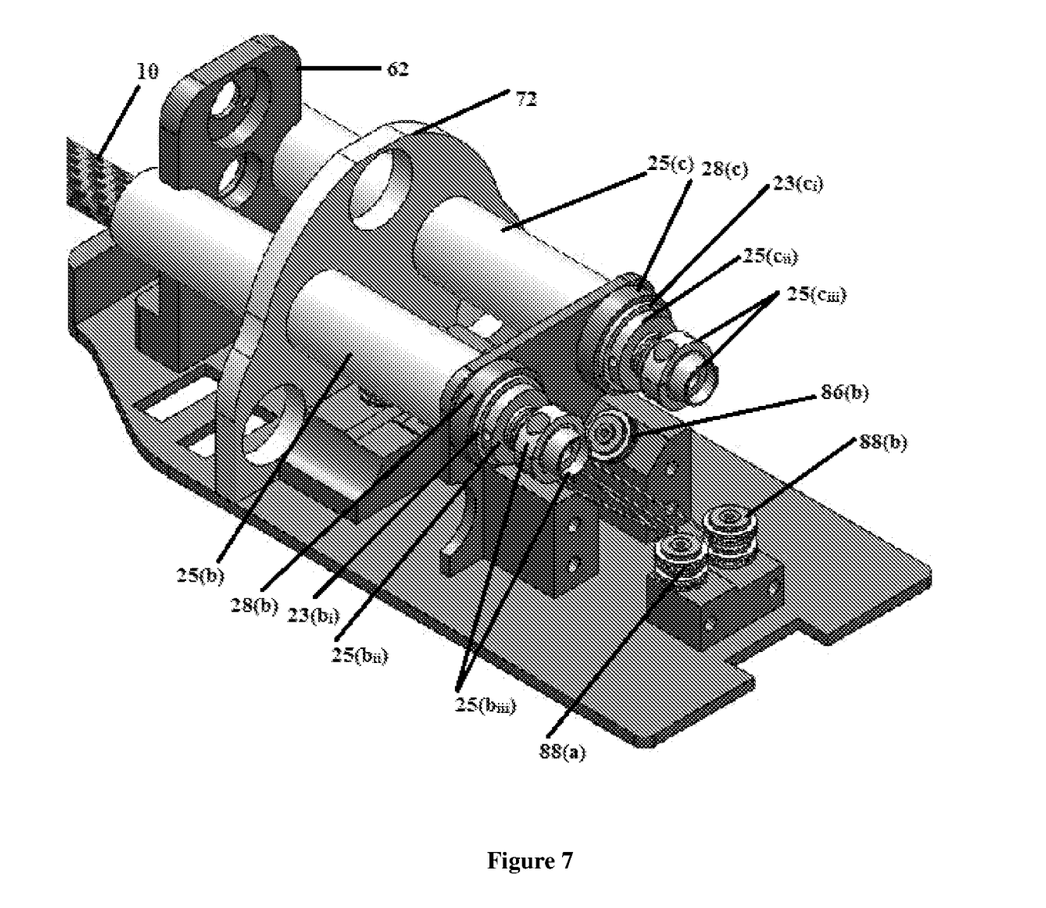
FIG. 7 illustrates placement of wrist member moving actuators in accordance with an embodiment of the present invention.

Now, as clearly shown in FIG. 6, the wrist member-moving elongate elements 38(a) and 38(b) then snugly travels towards the third compartment 80 where it wounds, at least partially around the guide pulleys 86(a) and 86(b) respectively before it gets anchored to wrist member moving actuators 25(b) and 25(c) respectively that controls rotation of the wrist member 30 about wrist axis 32 as shown in FIG. 7.

The actuators, in one preferred embodiment, are configured to include an elongated shaft 10 that is capable of mounting thereupon a multi-grooved pulley assembly fastened thereto by fastening mechanism e.g. by means of a grub screw or other suitable fastener that securely affixes the pulley assembly to the motor shaft. The multi-grooved pulley is further configured to receive the elongate element that wraps around the pulley and is pretensioned to at least half of maximum operating tension to eliminate any slack. The multi-grooved pulley, in one specific embodiment, includes on its peripherals a pair of identical disks that also remains fastened to the motor shaft by any suitable fastening mechanism. One of the disks of the two identical disks, preferably the one positioned outwardly towards the end of motor shaft, is a split disk that includes two semi-circular portions interlocked with each other by a fastening means to form a complete aperture disk. The upper semi-circular portion is typically a C-type pulley that is adapted to effectuate pretensioning of cable engaging therewith. The elongate element is pretensioned, up to a maximum of half the yield strength of the elongate element, to a level that avoids any segment thereof going slack at peak applied torque and avoids backlash.

In one significant aspect of the invention, the elongate element wounds around the multi-grooved pulley and is configured to slip through one opening and extend out from another opening provided on the multi-grooved pulley, following which in order to inhibit stretching of the elongate element along its length, an elongate relatively rigid member e.g. hypotube portions are introduced at the end of the elongate element extending out through the opening. The hypotube portions are then typically crimped in the ends to automatically lock the elongate member in the tensioned configuration. The hypotube is typically hollow tube having a cross-sectionally circular profile. Once the free end of elongate element is crimped, the C-type pulley is loosened slightly and counter-rotated to achieve pretensioning of the elongate element to a desired pulley.

In one preferred embodiment, on each side of the multi-grooved pulley assembly, a bearing 23, preferably ball bearing, rides on the actuator shaft secured thereto, and held therein by a mounting plate to prevent radial play of the pulley while the motor is in actuated state. Thus, referring to FIGS. 6 & 7, the wrist member moving elongate elements 38(a), 38(b) wounds around respective multi-grooved pulleys $25(b_i)$, $25(c_i)$ (not shown in Figure), with the ends of elongate elements configured to slip through openings on the multi-grooved pulleys $25(b_i)$, $25(c_i)$ and extend out to be introduced with hypotube portions and get pretensioned. This involves two identical disks around the peripherals of multi-grooved pulleys, $25(b_{ii})$, $25(b_{iii})$ and $25(c_{ii})$, $25(c_{iii})$ with one of the pulleys being a C-type pulley (as explained above)—$25(b_{iii})$, $25(c_{iii})$ to pretension the elongate elements. The multi-grooved pulleys $25(b_i)$, $25(c_i)$ further held by mounting plates 28(b), 28(c) and supported by pair of bearings $23(b_i)$, $23(b_{ii})$ and $23(c_i)$, $23(c_{ii})$.

In accordance with the mode of anchoring the elongate element to respective actuator, the free ends of wrist member moving elongate element 38(a) and 38(b) are guided through respective guide pulleys 86(a) and 86(b) to get snugly secured to respective actuators 25(b) and 25(c). Again, these guide pulleys are provided with ball bearings.

As indicated above, the free end of first working member moving elongate element 48(a) upon being partially guided by the topmost idler pulley of the urging arrangement $76(a_1)$ extends towards the proximal end of the carriage plate 20 to engage idler pulley $88(a_i)$ of the second guiding mechanism 88 before getting anchored to the respective multi-grooved pulley $25(d_i)$ [$25(d_{ii})$, $25(d_{iii})$] of the first elongate member moving actuator 25(d) that protrudes up to the third compartment. At the actuator 25(d), the elongate element gets pretensioned in a manner discussed above involving C-type pulley $25(d_{iii})$, mounting plate 28(d) and bearings $23(d_i)$ and $23(d_{ii})$.

In like manner, the other free end of the first working member moving elongate element 48(b) upon being partially guided by the bottommost idler pulley $76(b_{iii})$ of second composite pulley of the urging arrangement gets routed through an outer periphery of the second guide pulley 78(b) of the channeling structure 78 and advances into the third compartment to engage bottommost idler pulley $88(a_{ii})$ of the second guiding mechanism 88.

Now, the first end 48(a) and the second end 48(b) of the first working member moving elongate element gets anchored to the first working member-moving actuator 25(d) and gets pretensioned and secured thereto in a manner explained above.

In a similar fashion, the first free end of second working member moving elongate element 50(a) upon being partially guided by the topmost idler pulley of the urging arrangement $76(b_i)$ extends towards the proximal end of the carriage plate 20 to engage top laid idler pulley $88(b_i)$ of the second guiding mechanism 88 before getting anchored to the respective multi-grooved pulley $25(e_i)$ [$25(e_{ii})$, $25(e_{iii})$] of the second elongate member moving actuator 25(e) that protrudes up to the third compartment 80. At the actuator 25(e), the elongate element gets pretensioned in a manner discussed above by involving C-type pulley $25(e_{iii})$, mounting plate 28(e) and bearings $23(e_i)$ and $23(e_{ii})$.

Now, the other free end of the second working member moving elongate element 50(b) upon being partially guided by the bottommost idler pulley $76(a_{iii})$ of first composite pulley of the urging arrangement gets routed through an outer periphery of the first guide pulley 78(a) of the channeling structure 78 and advances into the third compartment to engage bottommost idler pulley $88(b_{ii})$ of the second guiding mechanism 88.

Thus, the first end 50(a) and the second end 50(b) of the second working member moving elongate element gets anchored to the second working member-moving actuator 25(e) and gets pretensioned and secured thereto in a manner explained above.

In one preferred embodiment of the present invention, the elongated elements are partially formed of a length of flexible cable and at least one hypotube portion that gets secured to one end of the flexible cable. Care should however be taken to prevent over-rotation of the instrument which would cause the cables to twist into contact with each other and create friction between the cables. In one other significant aspect of the invention, the actuators are sterilizable.

As is also depicted in FIG. 6, the ends of first and second working member moving elongate elements 48(a), 48(b), 50(a) and 50(b) arrange themselves in a decussate configuration such that minimal space yet maintaining a minimal separation from each other to prevent criss-crossing of elongate elements as they travel from urging arrangement towards their respective actuators. The distance between the elongate elements is maintained preferably, not less than 1 mm. From the given arrangement of elongate elements, it will be appreciated by those skilled in the art that the first and second working members are displaceable between open and close positions by decussate arrangement of elongate elements, in a scissor like fashion while the working members are biased towards the closed position.

Included in the concept of this invention are various modifications of the operable coupling between the actuating system 25, guiding mechanisms 78, 88 and elongate elements 38, 48 and 50 that can provide requisite actuation motions to the instrument, and will be apparent to those of ordinary skilled in the art. Therefore, it has to be understood that the specific engagements and combinations illustrated in given embodiments of the disclosure constitute only few possible embodiments for the purposes of explanation, and the invention is not meant to be limited by any particular combination.

Each actuator 25(a), 25(b), 25(c), 25(d) and 25(e) further includes magnetic encoders 31(a), 31(b), 31(c), 31(d) and 31(e) to enable motion control as they create close loop for motion that helps define trajectory of actuators to reset motion of the working members 48 & 50, as shown in FIG. 8. Further the carriage plate 20 supports printed circuit boards 33(a), 33(b), 33(c), 33(d) and 33(e) that is operably coupled to end of actuators 25(a), 25(b), 25(c), 25(d) and 25(e), and is further another printed circuit board is supported by the carriage plate 20 for energizing the actuators.

In at least embodiment, the surgical instrument, allows selective movement of the wrist member, the first and second working members by selective pulling of the corresponding elongate element in response to control signals applied thereto. The ends of each actuator are held by pulley holding plate that houses one of the bearings that secures the pulley.

Figure 9:
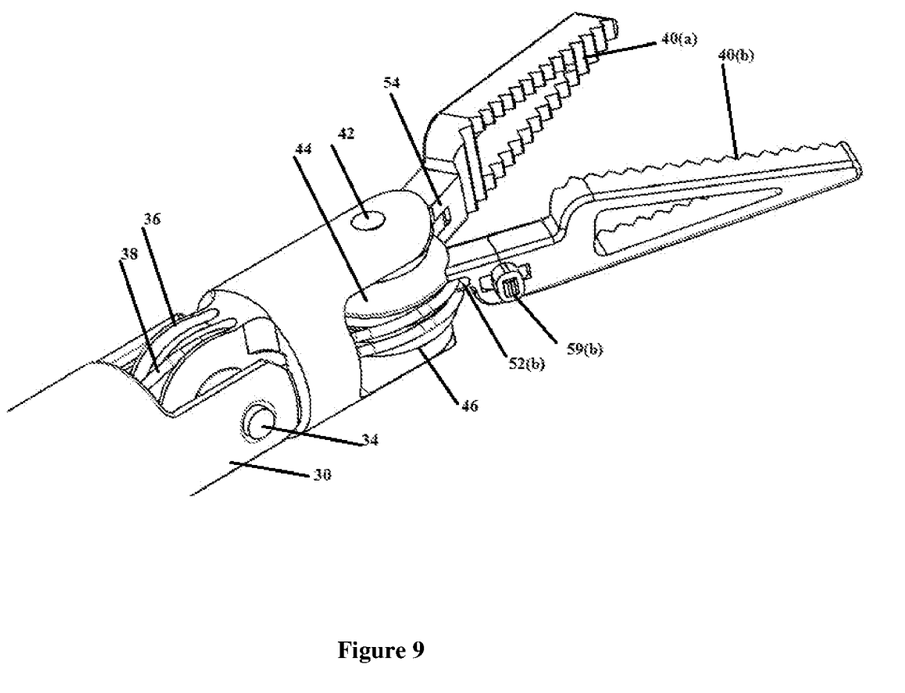
FIG. 9 is a perspective illustration of robotic surgical instrument having replaceable working members, in accordance with one embodiment of the present invention.

Now referring to FIG. 9, surgical instrument 100 having replaceable working members that allows substituting a more appropriate tip for a previous one for performing the same function, or for performing a different function relative to the wrist member 30 onto which the working members 40(a) and 40(b) are mounted, is presented. The newly replaced working members assure accurate positioning of the working tip and effect easy replacement or substitution of working members relative to the wrist member 30. The proposed mechanism enables all working members 40(a) and 40(b) of same or similar type to bear same working relationship with respect to wrist member 30, thus maintaining its working axis preferably orthogonal to wrist member axis.

In one illustrated embodiment of the surgical instrument 100 including a disposable or replaceable working members 40(a) and 40(b), allows close coupling or attachment of the working members with the wrist member 30, which for the purposes of explaining the effect of replacement of working member tips, shall be referred to as the receptacle over which the working members rest. The disposable or replaceable working members 40(a) and 40(b) may be used for cutting, shearing, grasping, engaging, or contacting tissue adjacent a surgical site.

In one general aspect, embodiments of the present invention provide a surgical instrument having replaceable working members that can control the lifetime of the surgical instrument more accurately.

Figure 10:
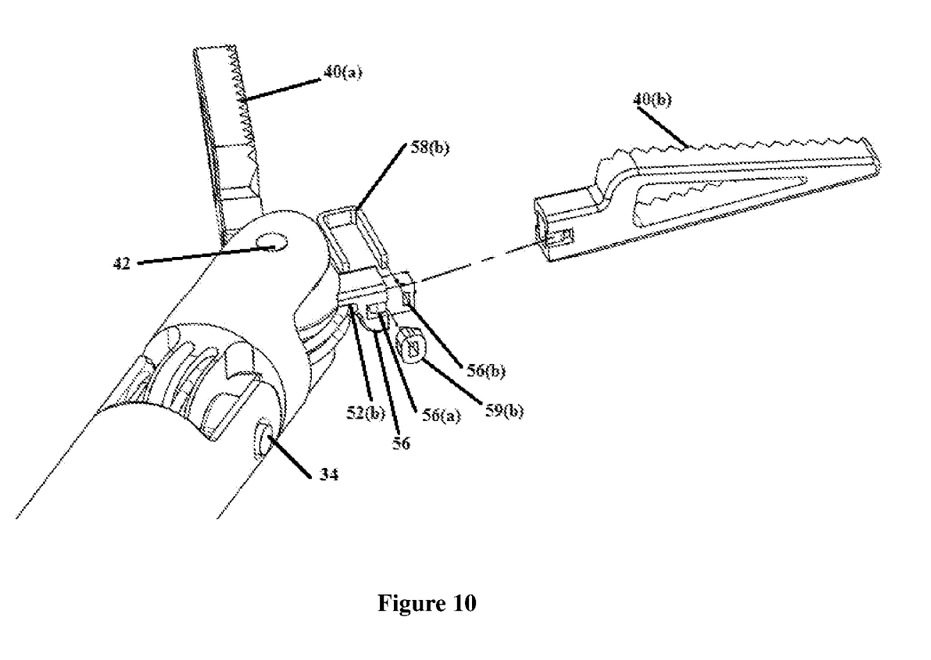
FIG. 10 is an exploded view of robotic surgical instrument having replaceable working members, in accordance with one embodiment of the present invention.

As discussed previously in the description, particularly in FIGS. 2 & 3, the working member axis, positioned orthogonally to wrist member axis 32 in space, is flanked by two set of pulleys 44 and 46 which are coaxially positioned on the pivotal connection 42 to be generally co-planar relative to each other. However, preferably as shown in FIGS. 9 and 10, the replaceable working member 40 is bipolar cautery instrument, wherein each working member is independently and removably coupled with respective pulley means, working member 40(a) with pulley means 46 and working member 40(b) with pulley means 44. While FIG. 9 depicts the working members 40 fixedly coupled with the respective pulley means, FIG. 10 is an exploded view that briefly explains the mechanism of coupling the pulley means with respective working members.

To enable an independent removable coupling, each pulley means 44 and 46 is designed to include respectively a relatively first square-like protrusion or block 54, 56 having disposed thereupon at least one relatively circular opening 52(a), 52(b) exhibiting an abutting relationship with adjacent pulley means 44, 46 respectively. The opening is sized to receive the elongate element 48, 50 unitarily with the pulley means 44 and 46 as shown in FIG. 10.

Again as seen in FIG. 10, the square-like protrusion or block 54, 56 includes second square—like protrusion which may be either a disengageable unit or may be integrally formed with square-like block 54, 56. For the purposes of illustration only, and by no means to restrict the scope of present disclosure, the first square-like block and the second square-like block are construed to be formed integrally with second square-like block being of size and dimensions relatively smaller than the first block 54, 56.

While the first-square like block 54, 56 further defines a slot 54(a), 56(a) toward its exterior surface, as shown in FIG. 10, the second-square like block also defines a slot 54(b), 56(b) towards its exterior surface such that an engaging member 58(a), 58(b) engages respectively the working member 40(a), 40(b) respectively with the pulley means 44 and 46. The second-square like block towards its end configured to engage with the working member defines an opening homogeneous with an opening provided at the coupling end of the working member such that the two opening are securely interconnected and are fixedly held therein by a suitable engaging member 58(a), 58(b).

The engaging member 58(a), 58(b), in one preferred embodiment is a flat or round stainless steel wire whose one free end is pushed through slot 54(a), 56(a) on the first-square like protrusion/block 54, 56 from exterior portion towards the interior, and reverse pulled through another slot 54(b), 56(b) provided on second-square like protrusion so as to tighten the stretch or span of wire. In other alternate arrangement, other flexible material exhibiting properties of high tensile strength and corrosion resistance.

A complementary arrangement, as indicated above, provided towards the coupling end of working member 40(a) and 40(b) includes a complementary opening of size and dimension that can fittedly engage with the slot 54(b), 56(b), such that the two attaching components now define a common unitary slot 54(b), 56(b) that receives the other end of engaging member, as defined above.

The two free ends of each engaging member, emerging towards the exterior, are now bundled or banded by applying a strapping material, a flexible material most commonly steel or plastic so as to ensure a tight fit. The straps, commonly designated as 59, and individually as 59(a) and 59(b) for working members 40(a) and 40(b) respectively, are locked conventionally by a lock which forms an integral part thereof. The engaging member 58 is preferably formed to have a rough, abrasive surface, at least towards its ends that gets bundled by the straps 59 to prevent slithering away of engaging member from locking strapping material.

Alternatively, in one other embodiment, the ends of engaging member 58(a), 58(b), may be pulled tightly and crimped by a portion of hypotube in a manner discussed in previous sections of the given detailed description.

In one other preferred embodiment, the inner surface of working members 40(a), 40(b) that shoulder each other during closing of the surgical instrument 100, is cut towards its coupling end in a receding flat surface to form an arcuate slot such that the engaging members 58(a), 58(b) running therethrough the slots 54(b), 56(b) respectively do not create any gap therebetween the working members in the closed position of the surgical instrument due to its thickness. The engaging member thus rests within the receding portion or the arcuate slot of the inwardly facing surface of the working member and never interferes with the closing and opening mechanism of the surgical instrument by pushing itself therebetween the tips of working members.

Figure 11:
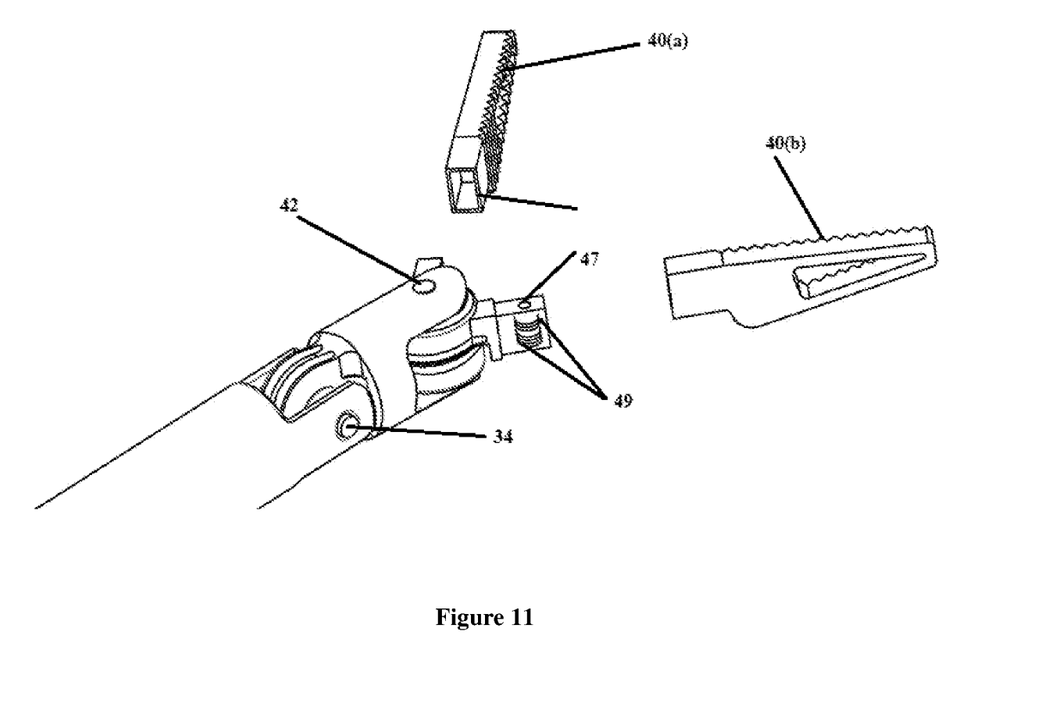
FIG. 11 illustrates yet another embodiment of robotic surgical instrument having replaceable working members.

Referring now to FIG. 11, the second-square like block of each working member 40(a), 40(b) on its side walls houses a steel ball 47, and within its housing accommodates a spring arrangement 49. The spring arrangement 49, in general, comprises one or more spring element or any other suitably selected resilient element that gets pressed or compressed when the working member is made to establish a snap-fit connection with the pulley means housing a slot. The coupling end of working member includes an opening that rides over the second-square like block and hence the steel balls 47, compresses the spring or resilient element 49 and snap-fit the components together in a secure linkage.

The foregoing description has been directed to one or more specific embodiments of the surgical instrument. It will be apparent; however, that other variations and modifications may be made to the described embodiments, with the attainment of some or all of their advantages. Accordingly this description is to be taken only by way of example and not to otherwise limit the scope of the invention, or depart from the basic inventive concepts. All such variations and modifications are to be considered within the scope of the present invention, the nature of which is to be determined from the foregoing description and the appended claims.

What is claimed is:

1. A surgical instrument comprising:
a longitudinal shaft having a shaft axis defining a proximal end and a distal end, the longitudinal shaft configured to be rotatable about the shaft axis;
a wrist member coupled to the distal end of the longitudinal shaft by a pivotal connection defining a wrist axis, the wrist member being angularly displaceable about the wrist axis by at least two wrist member-moving actuators operatively coupled to a single continuous wrist member-moving elongate element such that selective pulling of one end of the single continuous wrist member-moving elongate element causes concomitant movement of the wrist member therewith in one direction while counter-pulling causes movement of the wrist member in an opposed other direction; and
a first working member and a second working member coupled by a common pivotal connection to a working end of the wrist member to define a working member axis, and configured to be displaced angularly about the working member axis when independently actuated respectively by a first working member-moving actuator coupled with a corresponding first working member-moving elongate element or a second working member-moving actuator coupled with a corresponding second working member-moving elongate element,
wherein the first working member and the second working member are coupled with the respective working member-moving elongate elements by a snap-fit connection, wherein and the first working member and the second working member include an opening configured to receive a block of the respective working member-moving elongate element, and each block comprises a housing having one or more spring elements and at least one steel ball such that the steel ball compresses the one or more spring elements when the block is received by the opening of the first working member and the second working member.

2. The surgical instrument of claim 1, wherein the wrist axis and the working member axis are substantially orthogonal to each other.

3. The surgical instrument of claim 1, wherein each of the single continuous wrist member-moving elongate element, and the first and second working member-moving elongate elements are formed partially of a length of flexible cable and at least one hypotube portion secured to one end portion of the flexible cable, the single continuous wrist member-moving elongate element extending from the wrist member, and the first and second working member-moving elongate elements extending from the respective first working member and the second working member towards the proximal end of the shaft.

4. The surgical instrument of claim 1, further comprising an actuator for rotating the longitudinal shaft about the shaft axis.

5. The surgical instrument of claim 1, further comprising a carriage plate adapted to releasably secure the surgical instrument with a robotic arm of a minimally invasive surgical system.

6. The surgical instrument of claim 5, wherein the carriage plate is cooperatively engaged with the proximal end of the longitudinal shaft and houses the at least two wrist member-moving actuators, the first working member-moving actuator, the second working member-moving actuator and a longitudinal shaft rotating actuator that rotates the longitudinal shaft.

7. The surgical instrument of claim 6, wherein each of the actuators housed within the carriage plate are sterilizable.

8. The surgical instrument of claim 5, wherein the carriage plate further comprising composite pulley assembly arranged for urging portions of elongate elements extending out of the proximal end of the longitudinal shaft towards each other by a predetermined spacing to collectively keep them close to the longitudinal shaft axis.

9. The surgical instrument of claim 8, wherein the predetermined spacing corresponds to a distance not more than 1.4 mm.

10. The surgical instrument of claim 8, wherein the urging arrangement comprises at least two composite pulley assemblies, each composite pulley assembly further comprising a stack of at least three idler pulleys, wherein topmost idler pulleys of the stacks are configured to receive a first end of the first working member-moving elongate element and a first end of the second working member-moving elongate element respectively;
the central idler pulleys are configured to receive one end each of the single continuous wrist member-moving elongate element; and
the bottommost idler pulleys being configured to receive a second end of the first and second working member-moving elongate elements such that second working member-moving elongate element is received by the bottommost idler pulley of the stack of at least three idler pulleys whose topmost idler pulley receives the first end of first working member-moving elongate element and second end of first working member-moving elongate element is received by the bottommost idler pulley of the stack of at least three idler pulleys whose topmost idler pulley receives the first end of second working member-moving elongate element.

11. The surgical instrument of claim 1, wherein the first working member and the second working member are configured to be displaceable between open and close positions in a scissor-like fashion relative to each other, said working members being biased towards the closed position.

12. The surgical instrument of claim 1, wherein the single continuous wrist member-moving elongate element is wound around a pulley disposed at the wrist member, wherein free ends of the simile continuous wrist member-moving elongate element extend through the longitudinal shaft towards the proximal end of the longitudinal shaft, are urged by an urging arrangement so as to be routed over a pair of guide-pulleys and then anchored to the respective wrist member-moving actuators.

13. The surgical instrument of claim 12, wherein the pair of guide-pulleys are mounted at an angle with respect to the shaft axis of the longitudinal shaft in a manner so that each end of the single continuous wrist member-moving elongate element in received by the pair of guide-pulleys and routed towards the respective wrist member-moving actuators.

14. The surgical instrument of claim 13, wherein the pair of guide-pulleys are inclined at an angle between 30 degrees to 65 degrees relative to the shaft axis of the longitudinal shaft.

15. The surgical instrument of claim 12, wherein each of the wrist member-moving actuators comprises an actuator shaft having a multi-grooved pulley assembly mounted thereon, the multi-grooved pulley assembly configured to receive the single continuous wrist member-moving elongate element that is pretensioned to at least half of maximum operating tension to eliminate any slack in the single continuous wrist member-moving elongated element.

16. The surgical instrument of claim 15, the multi-grooved pulley receiving the single continuous wrist member-moving elongate element has disposed thereupon one or more spaced holes that are sized to receive the single continuous wrist member-moving elongate element, the single continuous wrist member-moving elongate element being further adapted to receive a hypotube that remains at least partially compressed to automatically lock the single continuous wrist member-moving elongated element in a tensioned configuration.

17. The surgical instrument of claim 15, wherein at least one bearing is mounted on the actuator shaft on either side of multi-grooved pulley assembly to reduce radial play of the multi-grooved pulley assembly.

18. The surgical instrument of claim 5, wherein at least two pulleys having diametrical portions are disposed at the wrist member and the first working member-moving element and the second working member-moving element are at least partially around the diametrical portions of the at least two pulleys respectively, wherein free ends of each of the first and second working member-moving elongate elements extend through the longitudinal shaft towards the proximal end of the longitudinal shaft and are urged towards each other by a predetermined spacing by an urging arrangement.

19. The surgical instrument of claim 18, wherein the first end of the first working member-moving element is wound at least partially around the topmost idler pulley of the first composite pulley assembly and extends towards a proximal end of the carriage plate and is guided over a second guiding mechanism and then anchored to the first working member-moving actuator.

20. The surgical instrument of claim 18, wherein the second end of the first working member-moving element is wound at least partially around the bottommost idler pulley of the second composite pulley assembly, is routed through an outer periphery of a second guide pulley that forms part of a channeling structure, guided by a second guiding mechanism and then anchored to the first working member-moving actuator.

21. The surgical instrument of claim 17, wherein the first end of the second working member-moving element is wound at least partially around a topmost idler pulley of a second composite pulley assembly, extends towards the proximal end of a carriage plate, guided by a second guiding mechanism and then anchored to the second working member-moving actuator.

22. The surgical instrument of claim 17, wherein the second end of the second working member-moving element is wound at least partially around a bottommost idler pulley of a first composite pulley assembly, routed through an outer periphery of a first guide pulley that forms part of a channeling structure, guided by a second guiding mechanism and then anchored to the second working member-moving actuator.

23. The surgical instrument of claim 20, wherein the second guiding mechanism includes a set of idler pulleys aligned in a stacked configuration wherein top laid idler pulleys of each set receive a first end of the first working member-moving elongate element and a first end of the second working member-moving element, and bottom laid idler pulleys of each set receive alternate second ends of working member-moving elongate elements such that a second end of the first working member-moving elongate element is received by a bottom laid idler pulley of the stack whose top laid idler pulley receives the first end of the second working member-moving elongate element, and a second end of the second working member-moving elongate element is received by a bottom laid idler pulley of the stack whose top laid idler pulley receives the first end of first working member-moving elongate element.

24. The surgical instrument of claim 23, wherein the first working member-moving elongate element received by the top laid idler pulleys is maintained in a different plane from that of second working member-moving elongate element received by a second set of idler pulleys, such that ends of each of the first working member-moving elongate elements and second working member-moving elongate elements are arranged in a decussate configuration, while maintaining a minimal separation to eliminate frictional engagement therebetween, whereby effectuating scissor like motion of the working members relative to each other.

25. The surgical instrument of claim 20, wherein the channeling structure comprises a first guide pulley and a second guide pulley that are maintained in a plane other than that of the urging arrangement, thereby being configured to channelize the second end of each of the second working member-moving elongate element and the second end of the first working member-moving elongate element through their outer periphery respectively, so as to prevent criss-crossing of the first and second working member-moving elongated elements as they extend towards the proximal end of the carriage plate.

26. The surgical instrument of claim 1, wherein each of the first and second working member-moving actuators comprise an elongated actuator shaft having a multi-grooved pulley assembly fastened thereto by a fastening mechanism, the multi-grooved pulley configured to receive the first and second working member-moving elongate elements, said first and second working member-moving elongate elements being pretensioned to at least half of maximum operating tensions to eliminate any slack.

27. The surgical instrument of claim 26, wherein the multi-grooved pulley includes on its peripherals identical disks fastened to a working member-moving actuator shaft, configured to effectuate pretensioning of the first and second working member-moving elongate elements.

28. The surgical instrument of claim 26, the multi-grooved pulley receiving the first and second working member-moving elongate elements comprises one or more spaced holes being sized to receive the first and second working member-moving elongate elements, said first and second working member-moving elongate elements being adapted further to receive a hypotube that remains at least partially compressed to automatically lock the first and second working member-moving elongate elements in a tensioned configuration.

29. The surgical instrument of claim 27, wherein the actuator shaft of each of the first and second working member-moving actuators include at least one bearing to reduce radial play of the multi-grooved pulley.

30. The surgical instrument of claim 5, wherein the carriage plate further houses an actuator drivingly engaged with a gear assembly to permit rotation of the longitudinal shaft about the shaft axis.

31. The surgical instrument of claim 30, wherein the gear assembly comprises two or more gears arranged in a stack configuration such that desired power is achieved by operable engagement of the gear assembly configuration with the actuator drivingly engaged with the gear assembly to permit rotation of the shaft.

32. The surgical instrument of claim 30, wherein the gear assembly includes plurality of spur gears having gear ratio of 1:1.

33. The surgical instrument of claim 6, wherein the first working member-moving actuator and the second working member-moving actuator are coupled to magnetic encoders that control movement of the first and second working members.

34. The surgical instrument of claim 1, wherein the first working member and the second working member are each independently and removably coupled with the respective first working member-moving elongate element and the second working member-moving elongate element.

35. The surgical instrument of claim 1, wherein the first working member and the second working member comprise a bipolar cautery instrument.

* * * * *